United States Patent [19]

Kawaguchi et al.

[11] Patent Number: 5,141,551

[45] Date of Patent: Aug. 25, 1992

[54] BENZOXAZINE DERIVATIVE AND BENZOTHIAZINE DERIVATIVE AND HERBICIDE COMPRISING THE SAME AS ACTIVE INGREDIENT

[75] Inventors: Naoko Kawaguchi, Moriguchi; Harukazu Fukami, Kyoto; Shinjiro Niwata, Ibaraki; Ryuichi Sago, Isehara; Fumio Fujita, Yokohama, all of Japan

[73] Assignee: Suntory Limited, Osaka, Japan

[21] Appl. No.: 631,978

[22] Filed: Dec. 21, 1990

[30] Foreign Application Priority Data

Dec. 22, 1989 [JP] Japan .................. 1-331095

[51] Int. Cl.$^5$ .................. C07D 265/36; C07D 279/16; C07D 413/10; A01N 43/84
[52] U.S. Cl. ............................. 71/88; 71/51; 71/52; 544/90; 544/91; 544/105
[58] Field of Search ............................. 544/105; 71/88

[56] References Cited

U.S. PATENT DOCUMENTS

| | | | |
|---|---|---|---|
| 3,862,180 | 1/1975 | Jernow et al. | 260/242 |
| 4,721,784 | 1/1988 | Combs | 544/105 |
| 4,885,024 | 12/1989 | Enomoto | 544/105 |
| 4,981,508 | 1/1991 | Strunk | 544/105 |

FOREIGN PATENT DOCUMENTS

| | | |
|---|---|---|
| 106816 | 10/1983 | European Pat. Off. |
| 243018 | 10/1987 | European Pat. Off. |
| 364141 | 10/1989 | European Pat. Off. |
| 270707 | 8/1989 | German Democratic Rep. |

OTHER PUBLICATIONS

Cox, J. Med. Chem. 17(10) 1125(1974).

Primary Examiner—Mark L. Berch
Attorney, Agent, or Firm—Burns, Doane, Swecker & Mathis

[57] ABSTRACT

A benzoxazine derivative and a benzothiazine derivative having the formula (I):

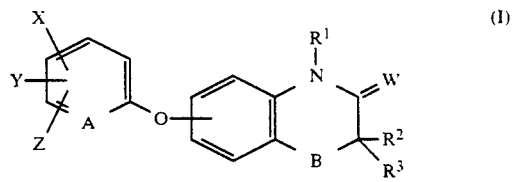

wherein
A is N or a CH group;
B is O, S, and SO group or an $SO_2$ group;
W is O, S, a $CR^4R^5$ group or an $NR^4$ group wherein $R^4$ and $R^5$ are each independently a hydrogen atom, a CN group or an $NO_2$ group;
X, Y and Z are each independently a hydrogen atom, a halogen atom or a lower haloalkyl group having 1 to 3 carbon atoms;
$R^1$ is a hydrogen atom, a lower alkyl group having 1 to 5 carbon atoms, a lower alkenyl group having 2 to 5 carbon atoms, a lower alkynyl group having 2 to 5 carbon atoms, a lower hydroxyalkyl group having 1 to 5 carbon atoms or a lower haloalkyl group having 1 to 3 carbon atoms; and
$R^2$ and $R^3$ are each independently a hydrogen atom, a lower alkyl group having 1 to 5 carbon atoms or an aryl group having 6 to 10 carbon atoms and a herbicidal composition containing the compound of the formula (I) as an active ingredient.

5 Claims, No Drawings

BENZOXAZINE DERIVATIVE AND BENZOTHIAZINE DERIVATIVE AND HERBICIDE COMPRISING THE SAME AS ACTIVE INGREDIENT

BACKGROUND OF THE INVENTION

1. Field of the Invention

The present invention relates to a benzoxazine derivative and a benzothiazine derivative having the formula (I):

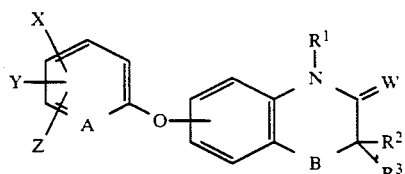

wherein
- A is N or a CH group;
- B is O, S, an SO group or an $SO_2$ group;
- W is O, S, a $CR^4R^5$ group or an $NR^4$ group wherein $R^4$ and $R^5$ are each independently a hydrogen atom, a CN group or an $NO_2$ group;
- X, Y and Z are each independently a hydrogen atom, a halogen atom or a lower haloalkyl group having 1 to 3 carbon atoms;
- $R^1$ is a hydrogen atom, a lower alkyl group having 1 to 5 carbon atoms, a lower alkenyl group having 2 to 5 carbon atoms, a lower alkynyl group having 2 to 5 carbon atoms, a lower hydroxyalkyl group having 1 to 5 carbon atoms or a lower haloalkyl group having 1 to 3 carbon atoms; and
- $R^2$ and $R^3$ are each independently a hydrogen atom, a lower alkyl group having 1 to 5 carbon atoms or an aryl group having 6 to 10 carbon atoms.

The present invention relates also to a herbicide comprising the same as an active ingredient.

In the substituents in the above-described general formula (I), examples of the halogen atoms in X, Y and Z include fluorine, chlorine and bromine atoms, and examples of the lower haloalkyl group include trifluoromethyl, difluoromethyl, trichloromethyl, dichloromethyl, tribromomethyl, dibromomethyl, trifluoroethyl, pentafluoroethyl, trichloroethyl, pentachloroethyl, tribromoethyl, pentabromoethyl, trifluoropropyl, trichloropropyl and tribromopropyl groups.

Examples of the lower alkyl group in $R^1$, $R^2$ and $R^3$ include methyl, ethyl, n-propyl, isopropyl, n-butyl, isobutyl and pentyl groups. Examples of the lower alkenyl group in $R^1$ include vinyl, allyl, isopropenyl and pentenyl groups, examples of the lower alkynyl group in $R^1$ include ethynyl, propynyl, butynyl and pentynyl groups, and examples of the lower hydroxyalkyl group in $R^1$ include hydroxymethyl, hydroxyethyl, hydroxypropyl and hydroxypentyl groups. Examples of lower haloalkyl group in R' include fluoromethyl, chloromethyl, bromomethyl, difluoromethyl, trifluoromethyl, and trifluoroethyl gruops.

Examples of the aryl group in $R^2$ and $R^3$ include phenyl and naphthyl groups.

2. Description of the Related Art

With respect to substituted phenoxybenzoxazinone derivatives, the following compound is described in, for example, J. Med. Chem. 17(10), 1125–1127:

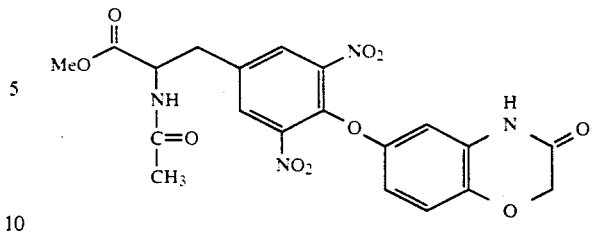

Nevertheless, no report has been made that states that substituted phenoxybenzoxazinone derivatives or substituted pyridyloxybenzoxazinone derivatives have a herbicidal activity.

SUMMARY OF THE INVENTION

Accordingly, the objects of the present invention are to develop a novel skeletal compound capable of suppressing the growth of various undesirable plants and a herbicidal composition comprising, as an active ingredient, the above-mentioned novel compound.

Other objects and advantages of the present invention will be apparent from the following description.

In accordance with the present invention, there is provided a novel compound having the above-mentioned formula (I) as a compound having a herbicidal activity.

In accordance with the present invention, there is also provided a herbicidal composition comprising the above-mentioned novel compound having the formula (I), as an active ingredient, and a carrier therefor.

DESCRIPTION OF THE PREFERRED EMBODIMENTS

Among the compounds having the above-mentioned formula (I), benzoxazinone derivatives and benzothiazinone derivatives can be prepared according to known methods. For example, a nitrobenzene derivative having the formula (II):

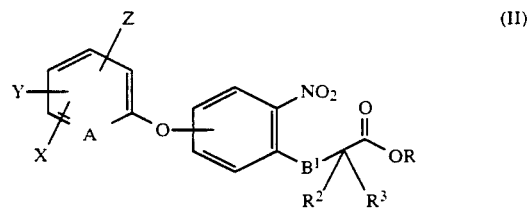

wherein A, X, Y, Z, $R^2$ and $R^3$ are as defined above, $B^1$ is an oxygen atom or a sulfur atom and R is a hydrogen atom or a lower alkyl group having 1 to 5 carbon atoms, can be reduced with a suitable reducing agent to prepare a compound having the formula (III):

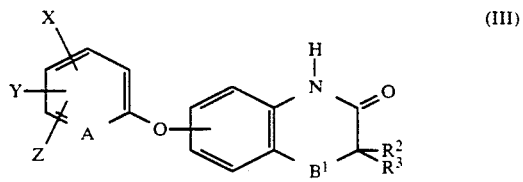

wherein A, $B^1$, X, Y, Z, $R^1$, $R^2$ and $R^3$ are as defined above.

The benzoxazinone derivative and benzothiazinone derivative can be reacted with a suitable alkylating agent, peracid, sulfiding agent or nucleophilic reagent alone, or if necessary in a combination of a plurality thereof, to prepare the benzoxazine derivative and benzothiazine derivative of the present invention.

Alternatively, some of the compounds of the present invention can be synthesized by the following method.

For example, a hydroxybenzoxazine derivative having the formula (IV):

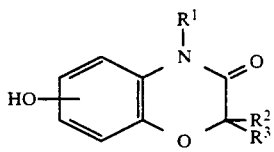
(IV)

wherein $R^1$, $R^2$ and $R^3$ are as defined above, may be reacted with a substituted benzene derivative or a substituted pyridine derivative having the formula (V):

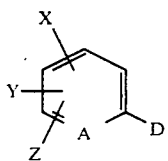
(V)

wherein A, X, Y and Z are as defined above and D is an eliminating group such as a halogen atom or a nitro group,
to prepare a compound having the formula (VI):

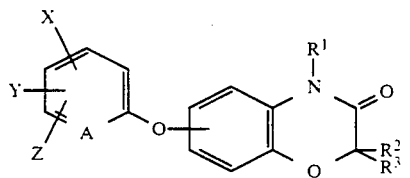
(VI)

wherein A, X, Y, Z, $R^1$, $R^2$ and $R^3$ are as defined above.

The compounds of the present invention have optical isomers derived from the above-mentioned substituents $R^2$ and $R^3$, and these isomers also fall within the scope of the present invention.

The compounds of the present invention prepared by the above-mentioned methods and having the formula (I) can be used as a herbicide before and after germination.

The compounds of the present invention are generally applied as a herbicide in combination with a suitable carrier. Examples of such carriers are solid carriers such as clay and diatomaceous earth, or liquid carriers such as water, alcohols, aromatic hydrocarbons, ethers, ketones and esters. If desired, emulsifying agents, dispersing agents, suspending agents, spreading agents and stabilizers may be added for the application of the compounds of the present invention in the form of emulsifiable concentrates, wettable powders, particles and granules. If necessary, the compounds of the present invention may be applied in the form of a mixture with, for example, various herbicides, various insecticides, fungicides, and plant growth regulators.

In practicing the present invention, although the concentration of the compounds of the present invention may be varied over a wide range, in general, preferably the concentration is 0.1 to 400 g per 10 a. Further, the above-mentioned various preparations may be prepared so as to have an active ingredient content of 0.5 to 90% by weight, more preferably 5 to 50% by weight.

EXAMPLES

The present invention will now be further illustrated by, but is by no means limited to the following Examples.

EXAMPLES 1 TO 5

7-(2-Chloro-4-trifluoromethylphenoxy)-2-methyl-2H-1,4-benzoxazine-3 (4H)-one (Example 1)

Methyl 2-[5-(2-chloro-4-trifluoromethylphenoxy)-2-nitrophenoxy]propionate (1.3 g) was dissolved in 10 ml of ethanol, raney nickel was added thereto as a catalyst, and a hydrogenation was then conducted. After the completion of the reaction, the reaction mixture was filtered and concentrated in vacuo, and the residue was purified by silica gel column chromatography (developing solvent: n-hexane/ethyl acetate=1/1) to prepare the title compound (0.9 g) as a colorless crystal (yield: 88%).

The following compounds were prepared in the same manner as described above.

7-(2-chloro-4-trifluoromethylphenoxy)-2H-1,4-benzoxazine-3 (4H)-one (Example 2);

7-(2-chloro-4-trifluoromethylphenoxy)-2,2-dimethyl -2H-1,4-benzoxazine-3 (4H)-one (Example 3);

7-(2-chloro-4-trifluoromethylphenoxy)-2-phenyl-2H-1,4-benzoxazine-3 (4H)-one (Example 4); and 7-(3-chloro-5-trifluoromethyl-2-pyridyloxy)-2-methyl-2H-1,4-benzoxazine-3 (4H)-one (Example 5).

EXAMPLES 6 TO 13

7-(2-Chloro-4-trifluoromethylphenoxy)-2,4-dimethyl-2H-1,4-benzoxazine-3 (4H)-one (Example 6)

First, 60% sodium hydride (0.2 g) was suspended in dimethylformamide (5 ml), and a solution of 7-(2-chloro -4-trifluoromethylphenoxy)-2-methyl-2H-1,4-benzoxazine-3 (4H)-one (0.4 g) prepared in Example 1 in dimethylformamide (5 ml) was dropwise added thereto while cooling with ice, and the mixture was stirred for 10 min. Then methyl iodide (0.7 g) was added thereto and the mixture was stirred for additional 10 min, and thereafter, water (20 ml) was added thereto to terminate the reaction. The reaction mixture was extracted with ethyl acetate (50 ml×2), washed with water and a saturated saline solution, and then dried over anhydrous magnesium sulfate. The solvent was distilled off in vacuo, and the residue was purified by silica gel column chromatography (developing solvent: n-hexane/ethyl acetate=3/1) to prepare the title compound (0.4 g) as a colorless crystal (yield: 98%).

The following compounds were prepared in the same manner as described above.

7-(2-chloro-4-trifluoromethylphenoxy)-4-ethyl-2-methyl-2H-1,4-benzoxazine-3 (4H)-one (Example 7);

7-(2-chloro-4-trifluoromethylphenoxy)-4-isopropyl-2-methyl-2H-1,4-benzoxazine-3 (4H)-one (Example 8);

7-(2-chloro-4-trifluoromethylphenoxy)-2-methyl-4-propynyl-2H-1,4-benzoxazine-3 (4H)-one (Example 9);

7-(2-chloro-4-trifluoromethylphenoxy)-4-methyl-2H-1,4-benzoxazine-3 (4H)-one (Example 10);

7-(2-chloro-4-trifluoromethylphenoxy)-2,2,4-trimethyl-2H-1,4-benzoxazine-3 (4H)-one (Example 11);

7-(2-chloro-4-trifluoromethylphenoxy)-2,4-dimethyl-2-phenyl-2H-1,4-benzoxazine-3 (4H)-one (Example 12);

7-(3-chloro-5-trifluoromethyl-2-pyridyloxy)-2,4-dimethyl-2H-1,4-benzoxazine-3 (4H)-one (Example 13);

EXAMPLE 14

7-(2-Chloro-4-trifluoromethylphenoxy)-4-hydroxymethyl-2-methyl-2H-1,4-benzoxazine-3 (4H)-one First, 7-(2-chloro-4-trifluoromethylphenoxy)-2-methyl-2H-1,4-benzoxazine-3 (4H)-one (0.4 g) prepared in Example 1 was dissolved in dioxane (5 ml), p-formaldehyde (0.1 g) and p-toluenesulfonic acid (0.1 g) were added to the solution, and the mixture was stirred at 80° C. for 3 hr. After the completion of the reaction, the reaction mixture was concentrated in vacuo, and the resultant residue was purified by silica gel column chromatography (developing solvent: n-hexane/ethyl acetate=1/1) to prepare the title compound (0.2 g) as a colorless crystal (yield: 50%).

EXAMPLES 15 AND 16

6-(2-Chloro-4-trifluoromethylphenoxy)-2-methyl-2H-1,4-benzoxazine-3 (4H)-one (Example 15)

In Example 1, methyl 2-[4-(2-chloro-4-trifluoromethylphenoxy)-2-nitrophenoxy]propionate was used instead of methyl 2-[5-(2-chloro-4-trifluoromethylphenoxy)-2-nitrophenoxy]propionate to prepare the title compound, and 6-(3-Chloro-5-trifluoromethyl-2-pyridyloxy)-2-methyl-2H-1,4-benzoxazine-3 (4H)-one (Example 16) was prepared in the same manner as described above.

EXAMPLES 17 AND 18

6-(2-Chloro-4-trifluoromethylphenoxy)-2,4-dimethyl-2H-1,4-benzoxazine-3 (4H)-one (Example 17)

In Example 6, 6-(2-chloro-4-trifluoromethylphenoxy)-2-methyl-2H-1,4-benzoxazine-3 (4H)-one was used instead of 7-(2-chloro-4-trifluoromethylphenoxy)-2-methyl-2H-1,4-benzoxazine-3 (4H)-one to prepare the title compound, and then 6-(3-Chloro-5-trifluoromethyl-2-pyridyloxy)-2,4-dimethyl-2H-1,4-benzoxazine-3 (4H)-one (Example 18) was prepared in the same manner as described above.

EXAMPLE 19

7-Phenoxy-2-methyl-2H-1,4-benzoxazine-3 (4H)-one

In Example 1, methyl 2-(5-phenoxy-2-nitrophenoxy)propionate was used instead of 2-[5-(2-chloro-4-trifluoromethylphenoxy)-2-nitrophenoxy]propionate, to prepare the title compound.

EXAMPLES 20 TO 22

7-(3,5-Dichlorophenoxy)-2-methyl-2H-1,4-benzoxazine-3 (4H)-one (Example 21)

First, 7-hydroxy-2-methyl-2H-1,4-benzoxazine-3 (4)-one (0.4 g) and 3,5-dichlorobromobenzene (0.5 g) were dissolved in dimethylsulfoxide (5 ml), anhydrous potassium carbonate (0.3 g) was added to the solution, and the mixture was heated at 100° C. for 1 hr. Water (20 ml) was added thereto to terminate the reaction, and the reaction mixture was extracted with ethyl acetate (30 ml×2) and then washed with water and a saturated saline solution. The washed extract was dried over anhydrous magnesium sulfate and the solvent was distilled off in vacuo, and the residue was purified by silica gel column chromatography (developing solvent: n-hexane/ethyl acetate=3/1) to prepare the title compound (0.2 g) as a colorless crystal (yield: 21%).

The following compounds were synthesized in the same manner as described above:
7-(2,6-dichloro-4-trifluoromethylphenoxy)-2-methyl-2H-1,4-benzoxazine-3 (4H)-one (Example 21); and
7-(2-chloro-6-fluoro-4-trifluoromethylphenoxy)-2-methyl-2H-1,4-benzoxazine-3 (4H)-one (Example 22).

EXAMPLES 23 TO 26

7-Phenoxy-2,4-dimethyl-2H-1,4-benzoxazine-3 (4)-one (Example 23)

In Example 6, 7-phenoxy-2-methyl-2H-1,4-benzoxazine-3 (4H)-one prepared in Example 19 was used instead of 7-(2-chloro-4-trifluoromethylphenoxy)-2-methyl-2H-1,4-benzoxazine-3 (4H)-one to prepare the title compound.

The following compounds were prepared in the same manner as described above:
7-(3,5-dichlorophenoxy)-2,4-dimethyl-2H-1,4-benzoxazine-3 (4H)-one (Example 24);
7-(2,6-dichloro-4-trifluoromethylphenoxy)-2,4-dimethyl-2H-1,4-benzoxazine-3 (4H)-one (Example 25); and
7-(2-chloro-6-fluoro-4-trifluoromethylphenoxy)-2,4-dimethyl-2H-1,4-benzoxazine-3 (4H)-one (Example 26).

EXAMPLE 27

7-(2-Chloro-6-fluoro-4-trifluoromethylphenoxy)-2-methyl-2H-1,4-benzothiazine-3 (4H)-one Reduced iron (1.3 g) was suspended in acetic acid (6 ml), a solution of 2-[5-(2-chloro-6-fluoro-4-trifluoromethylphenoxy)-2-nitrophenylthio]propionic acid (1.5 g) in acetic acid (2 ml) was added to the suspension, and the mixture was vigorously stirred for 20 hr. After the completion of the reaction, the reaction mixture was filtered and concentrated in vacuo, and the residue was extracted with ethyl acetate (50 ml×2), washed with water and a saturated saline solution and dried over anhydrous magnesium sulfate. The solvent was distilled off in vacuo, and the residue was purified by silica gel column chromatography (developing solvent: n-hexane/ethyl acetate=3/1) to prepare the title compound (0.9 g) as a colorless crystal (yield: 69%).

EXAMPLE 28

7-(2-Chloro-6-fluoro-4-trifluoromethylphenoxy)-2,4-dimethyl-2H-1,4-benzothiazine-3 (4H)-one In Example 6, 7-(2-chloro-6-fluoro-4-trifluoromethylphenoxy)-2-methyl-2H-1,4-benzothiazine-3 (4H)-one prepared in Example 27 was used instead of 7-(2-chloro-4-trifluoromethylphenoxy)-2-methyl-2H-1,4-benzoxazine-3 (4H)-one to prepare the title compound.

EXAMPLE 29

7-(2-Chloro-6-fluoro-4-trifluoromethylphenoxy)-2,4-dimethyl-2H-1,4-benzothiazone-3 (4H)-one-1-oxide m-Chloroperbenzoic acid (0.4 g) was added to a solution of 7-(2-chloro-6-fluoro-4-trifluoromethylphenoxy)-2,4-dimethyl-2H-1,4-benzothiazine-3 (4H)-one (0.8 g) prepared in Example 27 in methylene chloride (16 ml) while cooling with ice, and the mixture was stirred for 15 min. The reaction mixture was washed with water, a saturated aqueous sodium bicarbonate solution and a saturated saline solution, and dried over anhydrous magnesium sulfate. The solvent was distilled off in vacuo, and the residue was purified by silica gel column chromatography (developing solvent: n-hexane/ethyl acetate=1/1) to prepare the title compound (0.6 g) as a colorless crystal) (yield: 71%).

EXAMPLE 30

7-(2-Chloro-6-fluoro-4-trifluoromethylphenoxy)-2,4-dimethyl-2H-1,4-benzothiazine-3 (4H)-one-1-dioxide m-Chloroperbenzoic acid (0.8 g) was added at room temperature to a solution of 7-(2-chloro-6-fluoro-4-trifluoromethylphenoxy)-2,4-dimethyl-2H-1,4-benzothiazine-3 (4H)-one (0.8 g) in methylene chloride (27 ml), and the mixture was stirred for one hour. The reaction mixture was washed with water, a saturated aqueous sodium bicarbonate solution and a saturated saline solution and dried over anhydrous magnesium sulfate. The solvent was distilled off in vacuo, and the residue was purified by silica gel column chromatography (developing solvent: n-hexane/ethyl acetate=3/2) to prepare the title compound (0.6 g) as a colorless crystal (yield: 70%).

EXAMPLE 31

7-(2-Chloro-6-fluoro-4-trifluoromethylohenoxy)-4-difluoromethyl-2-methyl-2H-1,4-benzoxazine-3 (4H)-one First, 60% sodium hydride (0.1 g) was added to a solution of 7-(2-chloro-6-fluoro-4-trifluoromethylphenoxy)-2-methyl-2H-1,4-benzoxazine-3 (4H)-one (1.0 g) prepared in Example 22 in dimethylformamide (40 ml), and the mixture was stirred at room temperature for 30 min and cooled to −60° C. A chlorodifluoromethane gas was added by portions thereto, and the mixture was stirred at −60° C. for 5 hr and then at room temperature for 10 hr. Water was added thereto, and the reaction mixture was extracted with ethyl acetate and washed with a saturated sodium bicarbonate solution and a saturated saline solution. The washed extract was dried over anhydrous magnesium sulfate, the solvent was distilled off in vacuo, and the residue was purified by silica gel chromatography (developing solvent: n-hexane/ethyl acetate=9/1) to prepare the title compound (0.3 g) as a colorless oleaginous matter (yield: 27%).

EXAMPLE 32

7-(2-Chloro-6-fluoro-4-trifluoromethylphenoxy)-2(R),4-dimethyl-2H-1,4-benzoxazine-3 (4H)-one First, 60% sodium hydride (0.1 g) was suspended in dimethylformamide (10 ml), and a solution of 5-(2-chloro-6-fluoro-4-trifluoromethyl-phenoxy)-2-nitrophenol (1.1 g) in dimethylformamide (10 ml) was dropwise added thereto while cooling with ice, and the mixture was stirred for 20 min. Methyl (S)-2-chloropropionate (0.4 g) was added thereto, and the mixture was stirred at 80° C. for 2 hr, and thereafter, water (20 ml) was added thereto to terminate the reaction. The reaction mixture was extracted with ethyl acetate (50 ml×2), washed with water and a saturated saline solution and dried over anhydrous magnesium sulfate. The solvent was distilled off in vacuo, and the residue was purified by silica gel column chromatography (developing solvent: n-hexane/ethyl acetate=5/1) to prepare methyl 2(R)-[5-(2-chloro-6-fluoro-4- trifluoromethylphenoxy)-2-nitrophenoxy]propionate as a colorless oleaginous matter (0.4 g).

The methyl 2(R)-[5-(2-chloro-6-fluoro-4-trifluoromethylphenoxy)-2-nitrophenoxy]propionate (0.4 g) thus prepared was dissolved in ethanol (10 ml), a raney nickel catalyst was added thereto as a catalyst, and a hydrogenation was then conducted. After the completion of the reaction, the reaction mixture was filtered and concentrated in vacuo, and the residue was purified by silica gel column chromatography (developing solvent: n-hexane/ethyl acetate=3/1) to prepare 7-(2-chloro-4-trifluoromethylphenoxy)-2(R)-methyl-2H-1,4-benzoxazine-3 (4H)-one (0.3 g) as a colorless crystal.

Then, 60% sodium hydride (0.03 g) was suspended in dimethylformamide (5 ml), and a solution of the abovedescribed 7-(2-chloro-6-fluoro-4-trifluoromethylphenoxy)-2(R)-methyl-2H-1,4-benzoxazine-3 (4H)-one (0.3 g) in dimethylformamide (5 ml) was dropwise added thereto while cooling with water. The mixture was stirred for 10 min, methyl iodide (0.1 g) was added thereto, and the mixture was stirred for an additional 10 min. Water (10 ml) was added thereto to terminate the reaction, and the reaction mixture was extracted with ethyl acetate (20 ml×2), washed with water and a saturated saline solution and dried over anhydrous magnesium sulfate. The solvent was distilled off in vacuo, and the residue was purified by silica gel column chromatography (developing solvent: n-hexane/ethyl acetate=3/1) to prepare the title compound (0.3 g) as a colorless crystal. The compound thus prepared was subjected to HPLC analysis for chiral separation and found to be in agreement with the first eluted fraction in the case of racemate (Example 26) modification and have an optical purity of 80%.

EXAMPLE 33

7-(2-Chloro-6-fluoro-4-trifluoromethylphenoxy)-2(S),4-dimethyl-2H-1,4-benzoxazine-3 (4H)-one, optically active substance (1)

In Example 32, methyl (R)-2-chloropropionate was used instead of methyl (S)-2-chloropropionate to prepare the title compound. The compound thus prepared was subjected to HPLC analysis for chiral separation and found to be in agreement with the second eluted fraction in the case of racemate (Example 26) modification and have an optical purity of 70%.

EXAMPLE 34

7-(2-Chloro-4-trifluoromethylphenoxy)-2,4-dimethyl-2H-1,4-benzoxazine-3 (4H)-thione 7-(2-Chloro-4-trifluoromethylphenoxy)-2,4-dimethyl-2H-1,4-benzoxazine-3 (4H)-one (2.5 g) prepared in Example 6 was dissolved in toluene (30 ml), and 2,4-bis(4-methoxyphenyl)-1,3-dithia-2,4-diphosphetane-2,4-disulfide (1.9 g) was added thereto, and the resultant mixture was refluxed for 2 hr. The solvent was distilled off in vacuo, and the residue was purified by silica gel column chromatography (developing solvent: n-hexane/ethyl acetate=5/1) to prepare the title compound (2.9 g) as a colorless crystal.

EXAMPLES 35 AND 36

7-(2-Chloro-6-fluoro-4-trifluoromethylphenoxy)-2,4-dimethyl-2H-1,4-benzoxazine-3 (4H)-thione (Example 35)

First, 7-hydroxy-2,4-dimethyl-2H-1,4-benzoxazine-3 (4H)-thione (0.2 g) and 3-chloro-4,5-difluorotrifluoromethylbenzene (0.3 g) were dissolved in DMSO (5 ml), potassium carbonate (0.2 g) was added thereto, and the mixture was stirred at 80° C. for one hr. Water (10 ml) was added thereto to terminate the reaction, and the reaction mixture was extracted with ethyl acetate (20 ml×2), washed with water and a saturated saline solution and dried over anhydrous magnesium sulfate. The solvent was distilled off in vacuo, and the residue was purified by silica gel chromatography (developing solvent: n-hexane/ethyl acetate=5/1) to prepare the title compound (0.2 g) as a colorless crystal.

Then, 7-(2,6-dichloro-4-trifluoromethylphenoxy)-2,4-dimethyl-2H-1,4-benzoxazine-3 (4H)-thione (Example 36) was prepared in the same manner as that described above.

EXAMPLE 37

7-2-Chloro-4-trifluoromethylphenoxy)-2,4-dimethyl-3-nitromethYlene-2H-1,4-benzoxazine (Example 37)

First, 7-(2-Chloro-4-trifluoromethylphenoxy)-2,4-dimethyl-2H-1,4-benzoxazine-3 (4H)-thione prepared in Example 34 was dissolved in dimethoxyethane (10 ml), methyl triflate (0.3 g) was added thereto while cooling with ice, and the mixture was stirred for 3 hr to prepare a solution of the S-methylated compound. In another vessel, lithium dicyclohexylamide was prepared from dicyclohexylamine (0.4 g) and 1.6M n-butyl lithium (1.1 ml), nitromethane (0.1 g) was added to the lithium dicyclohexylamide under cooling on a dry ice-acetone bath, and the mixture was stirred at room temperature for 30 min and then added with ice cooling to the above-described solution of the S-methylated compound. The mixture was stirred at room temperature for 3 hr, water (10 ml) was added to terminate the reaction, and the reaction mixture was extracted with ethyl acetate (20 ml×2), washed with an aqueous ammonium chloride solution, water and a saturated saline solution, and dried over anhydrous magnesium sulfate. The solvent was distilled off in vacuo, and the residue was purified by silica gel column chromatography (developing solvent: n-hexane/ethyl acetate=5/1) to prepare the title compound (0.3 g) as a yellow crystal.

The following compounds were prepared in the same manner as described above.

7-(2-chloro-4-trifluoromethylphenoxy)-2,4-dimethyl-3-dicyanomethylene-2H-1,4-benzoxazine (Example 38);

7-(2-chloro-4-trifluoromethylphenoxy)-2,4-dimethyl-3-cyanoimine-2H-1,4-benzoxazine (Example 39);

7-(2-chloro-6-fluoro-4-trifluoromethylphenoxy)-2,4-dimethyl-3-nitromethylene-2H-1,4-benzoxazine (Example 40); and 7-(2,6-dichloro-4-trifluoromethylphenoxy)-2,4-dimethyl-3-nitromethylene-2H-1,4-benzoxazine (Example 41).

The properties of the compounds thus prepared are shown in Table 1.

TABLE 1

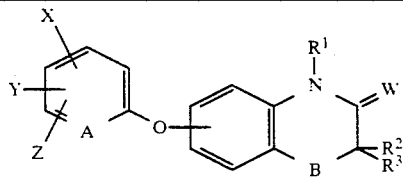

| Example No. | A | B | W | X | Y | Z | * | $R^1$ | $R^2$ | $R^3$ | Physical properties |
|---|---|---|---|---|---|---|---|---|---|---|---|
| 1 | CH | O | O | 2-Cl | 4-CF$_3$ | H | 7 | H | Me | H | m.p. 139–140.5° C. |
| 2 | CH | O | O | 2-Cl | 4-CF$_3$ | H | 7 | H | H | H | m.p. 179–180.5° C. |
| 3 | CH | O | O | 2-Cl | 4-CF$_3$ | H | 7 | H | Me | Me | m.p. 170–171° C. |
| 4 | CH | O | O | 2-Cl | 4-CF$_3$ | H | 7 | H | Ph | H | m.p. 162–163.5° C. |
| 5 | N | O | O | 3-Cl | 5-CF$_3$ | H | 7 | H | Me | H | m.p. 148–149.5° C. |
| 6 | CH | O | O | 2-Cl | 4-CF$_3$ | H | 7 | Me | Me | H | m.p. 81–84° C. |
| 7 | CH | O | O | 2-Cl | 4-CF$_3$ | H | 7 | Et | Me | H | m.p. 67–69° C. |
| 8 | CH | O | O | 2-Cl | 4-CF$_3$ | H | 7 | i-Pro | Me | H | m.p. 125–127.5° C. |
| 9 | CH | O | O | 2-Cl | 4-CF$_3$ | H | 7 | CH$_2$C≡CH | Me | H | m.p. 111–112.5° C. |
| 10 | CH | O | O | 2-Cl | 4-CF$_3$ | H | 7 | Me | H | H | m.p. 147–176° C. |
| 11 | CH | O | O | 2-Cl | 4-CF$_3$ | H | 7 | Me | Me | Me | m.p. 71.5–73° C. |
| 12 | CH | O | O | 2-Cl | 4-CF$_3$ | H | 7 | Me | Ph | Me | m.p. 163–164.5° C. |
| 13 | N | O | O | 3-Cl | 5-CF$_3$ | H | 7 | Me | Me | H | m.p. 77.5–79.5° C. |
| 14 | CH | O | O | 2-Cl | 4-CF$_3$ | H | 7 | CH$_2$OH | Me | H | $n_D^{25}$ 1.47480 |
| 15 | CH | O | O | 2-Cl | 4-CF$_3$ | H | 6 | H | Me | H | m.p. 175–176.5° C. |
| 16 | N | O | O | 3-Cl | 5-CF$_3$ | H | 6 | H | Me | H | m.p. 180.5–181.5° C. |
| 17 | CH | O | O | 2-Cl | 4-CF$_3$ | H | 6 | Me | Me | H | m.p. 71.5–73° C. |
| 18 | N | O | O | 3-Cl | 5-CF$_3$ | H | 6 | Me | Me | H | m.p. 103–105° C. |
| 19 | CH | O | O | H | H | H | 7 | H | Me | H | m.p. 149–151° C. |
| 20 | CH | O | O | 3-Cl | 5-Cl | H | 7 | H | Me | H | m.p. 189.5–190° C. |
| 21 | CH | O | O | 2-Cl | 4-CF$_3$ | 6-Cl | 7 | H | Me | H | m.p. 156–157.5° C. |
| 22 | CH | O | O | 2-Cl | 4-CF$_3$ | 6-F | 7 | H | Me | H | m.p. 149.5–151.5° C. |
| 23 | CH | O | O | H | H | H | 7 | Me | Me | H | $n_D^{25}$ 1.49080 |
| 24 | CH | O | O | 3-Cl | 5-Cl | H | 7 | Me | Me | H | m.p. 79–81° C. |
| 25 | CH | O | O | 2-Cl | 4-CF$_3$ | 6-Cl | 7 | Me | Me | H | m.p. 80–81.5° C. |
| 26 | CH | O | O | 2-Cl | 4-CF$_3$ | 6-F | 7 | Me | Me | H | $n_D^{25}$ 1.48176 |
| 27 | CH | S | O | 2-Cl | 4-CF$_3$ | 6-F | 7 | H | Me | H | m.p. 164–165.5° C. |
| 28 | CH | S | O | 2-Cl | 4-CF$_3$ | 6-F | 7 | Me | Me | H | $n_D^{25}$ 1.47620 |
| 29 | CH | SO | O | 2-Cl | 4-CF$_3$ | 6-F | 7 | Me | Me | H | m.p. 51–53° C. |
| 30 | CH | SO$_2$ | O | 2-Cl | 4-CF$_3$ | 6-F | 7 | Me | Me | H | m.p. 148–149° C. |
| 31 | CH | O | O | 2-Cl | 4-CF$_3$ | 6-F | 7 | CHF$_2$ | Me | H | $n_D^{25}$ 1.45460 |
| 32 | CH | O | O | 2-Cl | 4-CF$_3$ | 6-F | 7 | Me | Me | H | $n_D^{25}$ 1.48176 |
| 33 | CH | O | O | 2-Cl | 4-CF$_3$ | 6-F | 7 | Me | H | Me | $n_D^{25}$ 1.48176 |
| 34 | CH | O | S | 2-Cl | 4-CF$_3$ | H | 7 | Me | Me | H | m.p. 86–87° C. |
| 35 | CH | O | S | 2-Cl | 4-CF$_3$ | 6-F | 7 | Me | Me | H | m.p. 81.5–83.5° C. |
| 36 | CH | O | S | 2-Cl | 4-CF$_3$ | 6-Cl | 7 | Me | Me | H | m.p. 112–114° C. |
| 37 | CH | O | CHNO$_2$ | 2-Cl | 4-CF$_3$ | H | 7 | Me | Me | H | m.p. 145–147° C. |

TABLE 1-continued

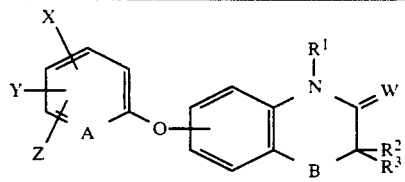

| Example No. | A | B | W | X | Y | Z | * | R¹ | R² | R³ | Physical properties |
|---|---|---|---|---|---|---|---|---|---|---|---|
| 38 | CH | O | C(CN)₂ | 2-Cl | 4-CF₃ | H | 7 | Me | Me | H | m.p. 163.5–164.5° C. |
| 39 | CH | O | N—CN | 2-Cl | 4-CF₃ | H | 7 | Me | Me | H | m.p. 144.5–145.5° C. |
| 40 | CH | O | CHNO₂ | 2-Cl | 4-CF₃ | 6-F | 7 | Me | Me | H | m.p. 164–165° C.(dec.) |
| 41 | CH | O | CHNO₂ | 2-Cl | 4-CF₃ | 6-Cl | 7 | Me | Me | H | m.p. 172.5–174° C. |

*The substituted portion of the phenoxy or pyridyloxy groups

TEST EXAMPLES

Test Example 1 (soil treatment)

Seeds of large crab-grass (*Digitaria adscendens Henr.*), foxtail (*Setaria viridis*), annual poa (*Poa annua L.*), purslane and smartweed (*Polygonum blumei Meisn.*) were planted in a seedling case having a size of 6 cm × 15 cm × 10 cm and packed with soil. On the day after seeding, the test compounds in the form of a 20% aqueous solution were diluted to 1/200 (one two hundredth) with water, and then applied to the surface of the soil, so that the dosage of the test compounds was 200 g per 10 a in terms of the active ingredient. Two weeks after the treatment with the test compounds, the herbicidal activity was measured by visible observation. (5: completely dead - 0: no herbicidal activity). The results are shown in Table 2.

TABLE 2

| Ex. No. | Herbicidal effect | | | | |
|---|---|---|---|---|---|
| | Large crab-grass | Fox-tail | Annual poa | Purs-lane | Smart-weed |
| 6 | 3 | 3.5 | 5 | 3.5 | 4.5 |
| 9 | 1.5 | 2 | 2 | 5 | 1.5 |
| 11 | 1 | 2 | 2 | 5 | 4.5 |
| 13 | 2.5 | 3 | 3.5 | 4.5 | 4 |
| 14 | 3 | 2 | 2.5 | 5 | 3 |

Test Example 2 (foliaqe treatment)

Seeds of large crab-grass (*Digitalia adscendens Henr.*), foxtail (*Setaria-viridis*), annual poa (*Poa annua L.*), purslane and smartweed (*Polygonum blumei Meisn.*) were planted in a seedling case having a size of 6 cm × 15 cm × 10 cm and packed with soil. After 10 day's culturing in a green house, aqueous solution, the test compounds in the form of a 20% wettable powder were diluted to 1/200 with water, and then applied to the surface of the foliage, so that the dosage of the test compounds was 200 g per 10 a in terms of the active ingredient. Two weeks after the treatment with the test compounds, the herbicidal activity was measured by visual observation (5: completely dead - 0: no herbicidal activity). The results are shown in Table 3.

TABLE 3

| Ex. No. | Herbicidal effect | | | | |
|---|---|---|---|---|---|
| | Large crab-grass | Fox-tail | Annual poa | Purs-lane | Smart-weed |
| 6 | 4 | 3.5 | 3 | 5 | 5 |
| 9 | 2.5 | 2 | 0 | 5 | 3 |
| 11 | 1.5 | 1.5 | 1 | 5 | 3 |
| 13 | 3.5 | 3.5 | 1.5 | 5 | 5 |
| 14 | 3 | 3 | 2 | 5 | 5 |

Test Example 3 (soil treatment)

Seeds of large crab-grass (*Digitaria adscendens Henr.*), umbrella plant (*Cyperus micro-iria*), pig weed (*Amaranphus lividus*), purslane (*Portulaca oleracea L.*) and smartweed (*Polygonum blumei Meisn.*) were planted in a seedling case having a size of 6 cm × 15 cm × 10 cm and packed with soil. On the day after seeding, test compounds in the form of a 20% aqueous solution were diluted to 1/800 with water, and then applied to the surface of the soil, so that the dosage of the test compounds was 50 g per 10 a in terms of the active ingredient. Two weeks after the treatment with the test compounds, the herbicidal activity was measured by visible observation (5: completely dead - 0: no herbicidal activity). The results are shown in Table 4.

TABLE 4

| Ex. No. | Herbicidal effect | | | | |
|---|---|---|---|---|---|
| | Large crab-grass | Pig weed | Purs-lane | Smart-weed | Umbrella plant |
| 26 | 4.5 | 5 | 5 | 5 | 5 |
| 29 | 3 | 2.5 | 5 | 4.5 | 4 |
| 31 | 5 | 5 | 5 | 5 | 5 |
| 32 | 5 | 5 | 5 | 5 | 5 |
| 35 | 2.5 | 5 | 5 | 5 | 5 |
| 40 | 1 | 5 | 5 | 3 | 5 |

Test Example 4 (foliaqe treatment)

Seeds of large crab-grass (*Digitaria adscendens Henr.*), umbrella plant (*Cyperus micro-iria*), pig weed, purslane (*Portulaca oleracea L.*) and smartweed (*Polygonum blumei Meisn.*) were planted in a seedling case having a size of 6 cm × 15 cm × 10 cm and packed with soil. After 10 day's culturing in a green house, test compounds in the form of a 20% aqueous solution were diluted to 1/800 (or one eight hundredth) with water, and then applied to the surface of the foliage so that the dosage of the test compounds was 50 g per 10 a in terms of the active ingredient. Two weeks after the treatment with the test compounds, the herbicidal activity was measured by visible observation. (5: completely dead - 0: no herbicidal activity). The results are shown in Table 5.

TABLE 5

| Ex. No. | Herbicidal effect | | | | |
|---|---|---|---|---|---|
| | Large crab-grass | Pig weed | Purs-lane | Smart-weed | Um-brella plant |
| 26 | 5 | 5 | 5 | 5 | 5 |
| 29 | 2 | 5 | 5 | 5 | 5 |
| 31 | 3 | 5 | 5 | 5 | 5 |
| 32 | 5 | 5 | 5 | 5 | 5 |
| 35 | 3 | 4.5 | 5 | 5 | 3.5 |
| 40 | 2 | 5 | 4.5 | 4.5 | 3 |

Test Example 5 (treatment before germination)

Seeds of barnyard grass (*Echinochloa oryzicok*), monochoria (*Monochoria vaginalis presl.*), small flower umbrella plant (*Cyperus difformis L.*), ammannia (Ammannia multiflora) and bulrush (*Scirpus juncoides Roxb.*) were planted in a polyvinyl chloride pack having a size of 16 cm × 11 cm × 6 cm, packed with soil, and filled with water. On the day after the seeding, acetone solutions of the test compounds (in some cases, an ethanol or aqueous solution) were diluted with water and then dropwise applied to the pack in an amount of 7.5 ml per pack, so that the dosage of the test compounds was 50 g per 10 a in terms of the active ingredient. Four weeks after the treatment with the test compounds, the herbicidal activity was measured by visible observation (5: completely dead - 0: no herbicidal activity). The results are shown in Table 6.

TABLE 6

| Ex. No. | Herbicidal effect | | | | |
|---|---|---|---|---|---|
| | Barn-yard grass | Mono-choria | Small flower umbrella | Ammannia | Bulrush |
| 25 | 5 | 5 | 5 | 5 | 3.5 |
| 26 | 5 | 5 | 5 | 5 | 4.5 |
| 29 | 5 | 5 | 5 | 5 | 1 |
| 31 | 5 | 5 | 5 | 5 | 1 |
| 32 | 5 | 5 | 5 | 5 | 4 |
| 35 | 5 | 5 | 5 | 5 | 2 |
| 40 | 5 | 5 | 5 | 5 | 4 |

Test Example 6 (treatment in growing season)

Seeds of barnyard grass (*Echinochloa oryzicock*), monochoria (*Monochoria vaginalis. pres.*), small flower umbrella plant (*Cyperus difformis L.*), ammannia (*Ammannia multiflora*) and bulrush (*Sciropus juncoides Roxb.*) were planted in a polyvinyl chloride pack having a size of 6 cm × 16 cm × 11 cm, packed with soil and filled with water. After two weeks' culturing, acetone solutions of the test compounds (in some cases, an ethanol or aqueous solution) were diluted with water, and then applied to the surface of the foliage in an amount of 7.5 ml per pack, so that the dosage of the test compound was 50 g per 10 a in terms of the active ingredient. Three weeks after the treatment with the test compounds, the herbicidal activity was measured by visible observation (5: completely dead - 0: no herbicidal activity). The results are shown in Table 7.

TABLE 7

| Ex. No. | Herbicidal effect | | | | |
|---|---|---|---|---|---|
| | Barn-yard grass | Mono-choria | Small flower umbrella | Ammannia | Bulrush |
| 25 | 3.5 | 3.5 | 5 | 5 | 3 |
| 26 | 5 | 5 | 5 | 5 | 4 |
| 29 | 3 | 4 | 5 | 5 | 1 |
| 31 | 4 | 4 | 5 | 4 | 1 |
| 32 | 5 | 5 | 5 | 5 | 4 |
| 35 | 3 | 5 | 5 | 5 | 1 |
| 40 | 5 | 5 | 5 | 5 | 2 |

[Preparation Examples]

Preparation Example 1 (emulsifiable concentrate)

First, 15 parts by weight of the compound of the present invention (for example, compound No. 25) as an active ingredient, 65 parts by weight of xylene and 20 parts by weight of polyoxyethylene alkylallyl ether were mixed to prepare a homogeneous solution, and thereby obtain an emulsifiable concentrate having an active ingredient content of 15%. The emulsifiable concentrate was diluted with water to a predetermined concentration prior to application.

Preparation Example 2 (wettable powder)

First, 40 parts by weight of the compound of the present invention (for example, compound No. 26) as an active ingredient, 55 parts by weight of Zieglite, 2 parts by weight of sodium alkylbenzenesulfonate, and 3 parts by weight of polyoxyethylene alkylaryl ether were mixed with each other and pulverized to prepare a wettable powder having an active ingredient content of 40%. The wettable powder was diluted with water, to a predetermined concentration, prior to application.

Preparation Example 3 (granule)

First, 5 parts by weight of the compound of the present invention (for example, compound No. 31) as an active ingredient, 73 parts by weight of clay, and 2 parts by weight of sodium dodecylbenzenesulfonate were mixed with each other. Then, about 20 parts by weight of water was added thereto and the mixture was kneaded with a kneader. The kneaded mixture was granulated with a granulator, dried, and graded to prepare a granule having an active ingredient content of 5%.

We claim:

1. A benzoxazine derivative having the formula (I):

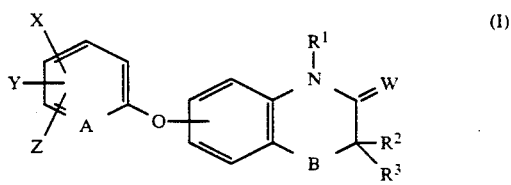

wherein

A is N or a CH group;

B is O:

W is O, S, a CR$^4$R$^5$ group or an NR$^4$ group wherein R$^4$ and R$^5$ are each independently a hydrogen atom, a CN group or NO$_2$ group;

X, Y and Z are each independently a hydrogen atom, a halogen atom or a lower haloalkyl group having 1 to 3 carbon atoms;

$R^1$ is a hydrogen atom, a lower alkyl group having 1 to 5 carbon atoms, a lower alkenyl gorup having 2 to 5 carbon atoms, a lower alkynyl group having 2 to 5 carbon atoms, a lower hydroxyalkyl group having 1 to 5 carbon atoms or a lwoer haloalkyl group having 1 to 3 carbon atoms; and $R^2$ and $R^3$ are each independently a hydrogen atom, a lower alkyl group having 1 to 5 carbon atoms or an aryl gorup having 6 to 10 carbon atoms.

2. A compound as claimed in claim 2, wherein in the formula (I);

A is CH,

W is O,

X, Y, and Z are each independently a hydrogen atom, a halogen atom, or a $CF_3$ group.

$R^1$ is a methyl or ethyl group, $R^2$ and $R^3$ are each independently a hydrogen atom, a methyl group or an ethyl group.

3. A herbicidal composition comprising as an active ingredient a compound according to claim 1, and a carrier therefor.

4. A herbicidal composition as claimed in claim 3 in the form of an emulsifiable concentrate, wettable powder, particle, dust or granule.

5. A herbicidal composition as claimed in claim 3, wherein the content of the active agent is 0.5 to 90% by weight.

* * * * *